(12) United States Patent
Wei et al.

(10) Patent No.: US 7,744,221 B2
(45) Date of Patent: Jun. 29, 2010

(54) METHOD OF EYE EXAMINATION BY OPTICAL COHERENCE TOMOGRAPHY

(75) Inventors: Jay Wei, Fremont, CA (US); Ben Jang, Cupertino, CA (US); David Huang, South Pasadena, CA (US); Yonghua Zhao, Fremont, CA (US)

(73) Assignee: Optovue, Inc., Fremont, CA (US)

( * ) Notice: Subject to any disclaimer, the term of this patent is extended or adjusted under 35 U.S.C. 154(b) by 0 days.

(21) Appl. No.: 11/656,075

(22) Filed: Jan. 19, 2007

(65) Prior Publication Data

US 2007/0195269 A1      Aug. 23, 2007

Related U.S. Application Data

(60) Provisional application No. 60/760,046, filed on Jan. 19, 2006, provisional application No. 60/782,888, filed on Mar. 17, 2006.

(51) Int. Cl.
*A61B 3/00* (2006.01)

(52) U.S. Cl. .................. 351/246; 351/206; 351/205; 351/200

(58) Field of Classification Search .............. 351/205, 351/209, 210, 246
See application file for complete search history.

(56) References Cited

U.S. PATENT DOCUMENTS

| | | | |
|---|---|---|---|
| 6,027,216 A | 2/2000 | Guyton et al. | |
| 6,293,674 B1 * | 9/2001 | Huang et al. | 351/221 |
| 7,480,058 B2 | 1/2009 | Zhao et al. | |
| 2004/0254474 A1 | 12/2004 | Seibel et al. | |
| 2005/0180622 A1 * | 8/2005 | Tan | 382/128 |
| 2006/0114414 A1 * | 6/2006 | McGrath et al. | 351/246 |
| 2007/0188765 A1 | 8/2007 | Zhao et al. | |

OTHER PUBLICATIONS

Ferguson, R. Daniel et al., "Three-Dimensional Retinal Maps With Tracking Optical Coherence Tomography (TOCT)," Proc. of SPIE, Jan. 2005, vol. 5690:66-71.
Koozekanani, Dara et al., "Tracking the Optic Nerve Head in OCT Video Using Dual Eigenspaces and an Adaptive Vascular Distribution Model," 2001 IEEE Computer Society Conference on Computer Vision and Pattern Recognition, Dec. 8-14, 2001, vol. 1:I934-I941.
Kulkarni, Manish D. et al. "Automated Optic-Nerve-Head Analysis Using Optical Coherence Tomography," Proceedings of SPIE, Jun. 2002, vol. 4619:237-239.
Mujat, Mircea et al., "Retinal Nerve Fiber Layer Thickness Map Determined by Optical Coherence Tomography Images," Optics Express, Nov. 7, 2005, vol. 13(23):9480-9491.

(Continued)

*Primary Examiner*—Joseph Martinez
*Assistant Examiner*—James R Greece
(74) *Attorney, Agent, or Firm*—Haynes and Boone, LLP

(57) ABSTRACT

A method of performing an OCT image scan is presented. Other images are taken and a template is formed to correct the OCT images, for example, for eye motion, blood vessel placement, and center offset. In some embodiments, video images are taken simultaneously with the OCT images and utilized to correct the OCT images. In some embodiments, a template OCT image is formed prior to acquisition of the OCT images and the template OCT image is utilized as a template from which to correct all of the OCT images.

18 Claims, 11 Drawing Sheets

OTHER PUBLICATIONS

Rohrschneider, Klaus et al., "Reproducibility of the Optic Nerve Head Tomography with a New Laser Tomographic Scanning Device," Journal of the American Academy of Ophthalmology, Jun. 1994, vol. 101(6):1044-1049.

Schuman, Joel S. et al., "Imaging of the Optic Nerve Head and Nerve Fiber Layer in Glaucoma," Ophthalmology Clinics of North America, Jun. 1995, vol. 8(2):259-279.

Webb, Robert H. et al., "Confocal Scanning Laser Ophthalmoscope," Applied Optics Apr. 15, 1987; vol. 26(8):1492-1497.

Weinreb, Robert et al., "Detection of Glaucoma With Scanning Laser Polarimetry," ARCH Ophthalmol, Dec. 1998, vol. 116:1583-1589.

Application as filed in U.S. Appl. No. 11/656,075.

Koozekanani, Dara et al., "Tracking the Optic Nervehead in OCT Video Using Dual Eigenspaces and an Adaptive Vascular Distribution Model", *IEEE Transactions on Medical Imaging*, vol. 22, No. 12, December 2003, pp. 1519-1536.

International Search Report and Written Opinion dated Oct. 15, 2007, in related International Application No. PCT/US07/01617.

Notice of Allowance mailed Sep. 12, 2008, in related U.S. Appl. No. 11/656,222.

Ferguson, R. Daniel et al., "Three-Dimensional Retinal Maps With Tracking Optical Coherence Tomography (TOCT)," Proc. of SPIE, Jan. 2005, vol. 5690:66-71.

Koozekanani, Dara et al., "Tracking the Optic Nerve Head in OCT Video Using Dual Eigenspaces and an Adaptive Vascular Distribution Model," 2001 IEEE Computer Society Conference on Computer Vision and Pattern Recognition, Dec. 8-14, 2001, vol. 1:1934-1941.

Kulkarni, Manish D. et al. "Automated Optic-Nerve-Head Analysis Using Optical Coherence Tomography," Proceedings of SPIE, Jun. 2002, vol. 4619:237-239.

Mujat, Mircea et al., "Retinal Nerve Fiber Layer Thickness Map Determined by Optical Coherence Tomography Images," Optics Express, Nov. 7, 2005, vol. 13(23):9480-9491.

Rohrschneider, Klaus et al., "Reproducibility of the Optic Nerve Head Tomography with a New Laser Tomographic Scanning Device," Journal of the American Academy of Ophthalmology, Jun. 1994, vol. 101(6):1044-1049.

Schuman, Joel S. et al., "Imaging of the Optic Nerve Head and Nerve Fiber Layer in Glaucoma," Ophthalmology Clinics of North America, Jun. 1995, vol. 8(2):259-279.

Webb, Robert H. et al., "Confocal Scanning Laser Ophthalmoscope," Applied Optics Apr. 15, 1987; vol. 26(8):1492-1497.

Weinreb, Robert et al., "Detection of Glaucoma With Scanning Laser Polarimetry," ARCH Ophthalmol, Dec. 1998, vol. 116:1583-1589.

Application as filed in U.S. Appl. No. 11/656,075, 2007.

* cited by examiner

Optic Nerve Head Analysis Results

Vert. Integrated Rim Area (Vol.)    $0.004m^2$
Horiz. Integrated Rim Width (Area) $1.003m^2$
Disk Area    $2.293m^2$
Cup Area    $1.436m^2$
Rim Area    $0.856m^2$
Cup/Disk Area Ratio    0.626
Cup/Disk Horiz. Ratio    0.782
Cup/Disk Vert. Area    0.023

METHOD OF EYE EXAMINATION BY OPTICAL COHERENCE TOMOGRAPHY

RELATED APPLICATION

The present application claims priority to Provisional Application No. 60/760,046, filed on Jan. 19, 2006, by Jay Wei, Ben Jang, and David Huang, and to Provisional Application No. 60/782,888, filed on Mar. 17, 2006, by Jay Wei, Ben Jang, David Huang, and Yonghua Zhao, each of which are herein incorporated by reference in their entirety.

BACKGROUND

1. Field of the Invention

The present invention is related to a method of performing an eye examination utilizing optical coherence tomography (OCT).

2. Discussion of Related Art

Retinal imaging by conventional optical image methodology, such as fundus camera imaging and indirect ophthalmoscopic imaging, has been routinely used clinically to evaluate retinal structure change. Routine retinal imaging provides valuable information for a clinician to diagnosis a number of eye diseases, including glaucoma. When there is a need to evaluate the optic nerve head tissue structure changes for glaucoma patients, stereoscopic retinal images are required to detect volumetric changes in the three dimensional nerve head structure. However, to date an experienced clinician can only provide a qualitative interpretation of eye structural changes from the retinal photograph.

Several imaging methods have been explored to quantitatively measure the three-dimensional structure of the nerve head. The Glaucoma Scope made by Ophthalmic Imaging Systems, Sacramento, Calif., used a technique of computed raster stereography. The Glaucoma Scope projected a series of equidistant, parallel, straight line beams of light onto the nerve head at oblique angles. By measuring the amount of deflection of the lines of light, nerve head topography can be determined. From the topographic view of the nerve head, many clinically significant volumetric parameters can be derived, such as disk area, cup area, disk rim area, and retinal nerve fiber layer (RNFL) thickness on the disk margin.

The Heidelberg Retinal Tomography (HRT), produced by Heidelberg Engineering, Germany, is based on a Laser Scanning Ophthalmoscope, SLO. By moving the focus plane of the scanning beam in the SLO, the topography of the nerve head can be measured. However, tissues like the choroid layer, which is underneath the superficial retinal surface layer, can not be seen with the SLO methods. As a result, the topography of the optical nerve layer is indirectly measured utilizing an artificial reference plane. Even with these advanced techniques, the ability to sufficiently map the optic nerve layer is limited. Further, the disk margin, which is also inside the retinal nerve fiber layer, is difficult to be accurately outlined by the SLO image. The accuracy of determining nerve head changes is limited.

A glaucoma exam, GDx, produced by Laser Diagnosis Technology, San Diego, Calif. is another method for mapping the RNFL. The GDx technique is based on polarimetry. The RNFL tissue is birefrigent and will cause polarization rotation as the probing beam of light passes through the RNFL. The thickness of the RNFL is indirectly measured by measuring the magnitude of the polarization rotation as the light beam is scanned across the retina. The RNFL thickness map is obtained by scanning the laser beam on the nerve head region. There are also disadvantages with GDX diagnosis. The cornea tissue is also birefrigent, which will add to the polarization rotation. The magnitude of polarization rotation by the cornea depends on the cornea thickness and light beam incident angle. The RNFL thickness accuracy significantly depends on the individual subjects to be measured.

Optical Coherence Tomography (OCT) is a new image modality that has been used for non-invasive human eye retinal imaging. A cross sectional retinal image taken while the beam is scanned across the retina allows the clinician to quantitatively evaluate the retinal nerve layer and retinal thickness. By composing radial line scan patterns, a 3-D nerve head geometry can be derived. An OCT system produced by Carl Zeiss Meditec, Dublin, Calif., for example, scans six radial lines passing across the nerve head. Volumetric parameters like disk area, cup area, and disk rim area are derived from these radial line images. Conventionally, the RNFL thickness is measured in a circular scan at a diameter of 3.45 mm centered on the center of the disk. OCT is advantageous over previous methods because OCT provides a direct measurement of the tissue thickness and does not significantly depend on other ocular tissue conditions. However, the sampling density is low compare to the other imaging methods and there are artifacts of the measurements resulting from slow scan speeds. Also, the RNFL thickness by a circular scan around the disk is often not reliable due to the off centering of the scan caused by inaccurate visual alignment and eye motion. The complete mapping of the retina nerve head volumetric parameters and RNFL around the nerve head region is usually unobtainable due to eye motion during the scan.

A complete mapping of the nerve head by OCT imaging has been possible only if the eye is fixed without any motion and there is no obscuration of the OCT scan beam so that important nerve head tissue are all visible in the OCT image. However, neither of these assumptions are feasible in a human subject.

Several attempts have been made to track the scan beam with the retina in order to eliminate the effects of eye motion. Dan Ferguson (Physical Science Inc, Andover, Mass.) utilized active feedback to track the scan beam on the retina based on a reflectometry principle. This method provides real-time tracking capability and has potential to scan completely over the nerve head. However, the extra confocal scanning laser hardware that needs to be added to the OCT scanner to perform this tracking method is complicated and expensive. Further, during a blink of the patient's eye, the tracking signal is lost and may not be recoverable from the previous scan sequence.

Another method of compensating for eye motion has been proposed by Dara Koozekanani (The Ohio State University, Columbus, Ohio). This method uses a combination of the reflected signal of the scan beam and a video image to register the retinal position. However, it is unclear as to use of this method for mapping the clinically significant nerve head parameters. Using raster line OCT scans to acquire three dimensional data sets for mapping of the retinal layer thickness has been described by Mujat et al in Optical Express. However, no description of how to map the nerve head boundary contour, which is essential as a reference for deriving all nerve head morphologic parameters, has been provided.

There is a need for direct measurement of all nerve head volumetric parameters, with complete mapping of the RNFL around the nerve head. Further, there is a need for acquiring and displaying all clinically significant information corresponding to the nerve head morphology that are highly desired by clinicians for diagnosing diseases such as glaucoma.

SUMMARY

In accordance with embodiments of the present invention, OCT images taken over a scan pattern are corrected utilizing one or more images. As such, a method of eye examination according to some embodiments of the present invention includes acquiring OCT images corresponding to a scan pattern, wherein the scan pattern substantially covers a nerve head region; determining disk boundary points from the OCT images; matching the disk boundary points with the disk boundary determined from one or more template images; correcting the disk boundary points; and determining at least one nerve head morphology characterization.

In some embodiments, the scan pattern includes a plurality of concentric circles and a plurality of radial lines. In some embodiments, correcting the disk boundary points includes performing a blood vessel correction. In some embodiments, correcting the disk boundary points includes determining a disk center. In some embodiments, determining at least one nerve head morphology characterization includes determining retinal nerve fiber layer thickness in a circle centered on the disk center. In some embodiments, the one or more template images are video images taken simultaneously with the OCT images. In some embodiments, correcting the disk boundary points includes correcting for eye movement. In some embodiments, the one or more template images is a template OCT image taken with a raster scan pattern. In some embodiments, a nerve head boundary is determined in the template OCT image.

These and other embodiments of the invention are further discussed below with reference to the following figures. It is to be understood that both the foregoing general description and the following detailed description are exemplary and explanatory only and are not restrictive of the invention, as claimed. Further, specific explanations or theories regarding the deposition or performance of certain layers during deposition processes or in the performance of devices incorporating those layers are presented for explanation only and are not to be considered limiting with respect to the scope of the present disclosure or the claims.

In the figures, elements having the same designation have the same or similar functions.

DETAILED DESCRIPTION

Embodiments of the current invention can be utilized for evaluating the eye tissue structure for diagnosing eye diseases. Some embodiments utilize an Optical Coherence Tomography (OCT) image, a fundus image, and an algorithm associated with both image modalities to map out the eye tissue structure accurately. Some embodiments of the invention provide an image of the eye tissue structure substantially absent of artifacts caused by eye motion or image distortion caused by light absorption of the retinal blood vessels. The current disclosed eye examination methods can be utilized in the diagnoses of eye pathologies in the optic nerve head, for example Glaucoma.

Figure 1A:
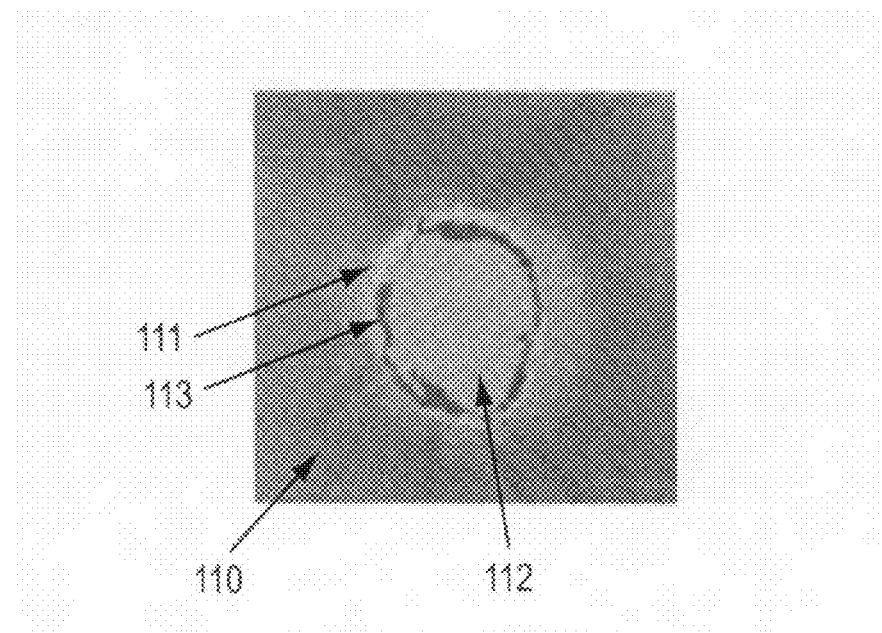
FIGS. 1A and 1B show images of the nerve head taken by the Heidelberg Retinal Tomography (HRT) technique.
Figure 1B:
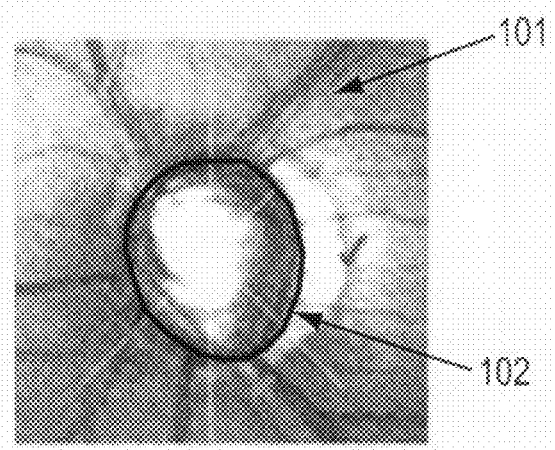

As discussed above, diagnosis of retinal eye pathologies depends on accurate and complete imaging of the nerve head area. Images of the nerve head area are shown in FIGS. 1A, 1B, 2A, 2B, and 3. FIGS. 1A and 1B were acquired with the HRT technique, FIGS. 2A and 2B were acquired with the GDx Technique, and FIG. 3 was acquired with an OCT technique. Each one of these images illustrates difference aspects of characterizing the nerve head.

FIGS. 1A and 1B shows an image 110 of the optic nerve head disk characterized by disk contour 111, and cup 112. The disk and cup shapes shown in FIGS. 1A and 1B are derived from a scanning laser confocal image device by HRT (Heidelberg Retinal Tomography, Heidelberg Engineering, Germany). As discussed above, the HRT technique scans the focal plane of a Laser Scanning Opthalmoscope (SLO) across the nerve head.

The disk contour 102 shown in FIG. 1B is drawn by an operator on the confocal retinal image 101. The shape of cup 112 is derived from a reference plane and the disk contour at that plane. The rim area 113 shown in image 110 of FIG. 1A is the area between the disk contour 111 (drawn as contour 102 on retinal image 101) and cup 112. The ratio of rim area 113 and the area enclosed by disk contour 111, the disk area, is a clinically significant parameter for glaucoma diagnosis. However, the reference plane is an important parameter for defining the disk area and thereby determining the rim to disk ratio calculation, and it is arbitrarily defined as 50 µm below the peripapillary retinal surface. Height variation of the retinal surface, which is often seen in ocular diseases, causes reference plane changes and therefore will change the calculated disk and cup parameters. Calculations of disk and cup parameters can therefore be unreliable utilizing this technique.

Another important parameter that is utilized in the diagnosis of optic nerve pathologies is the retinal nerve fiber layer (RNFL) thickness. The RNFL thickness is typically determined by the retinal height above the reference plane. A display (not shown with FIGS. 1A and 1B) of the retinal height along the disk margin is usually plotted as the variation of the RNFL thickness plot. Therefore, the RNFL thickness plots determined by the HRT technique are not accurate.

Figures 2A, 2B:
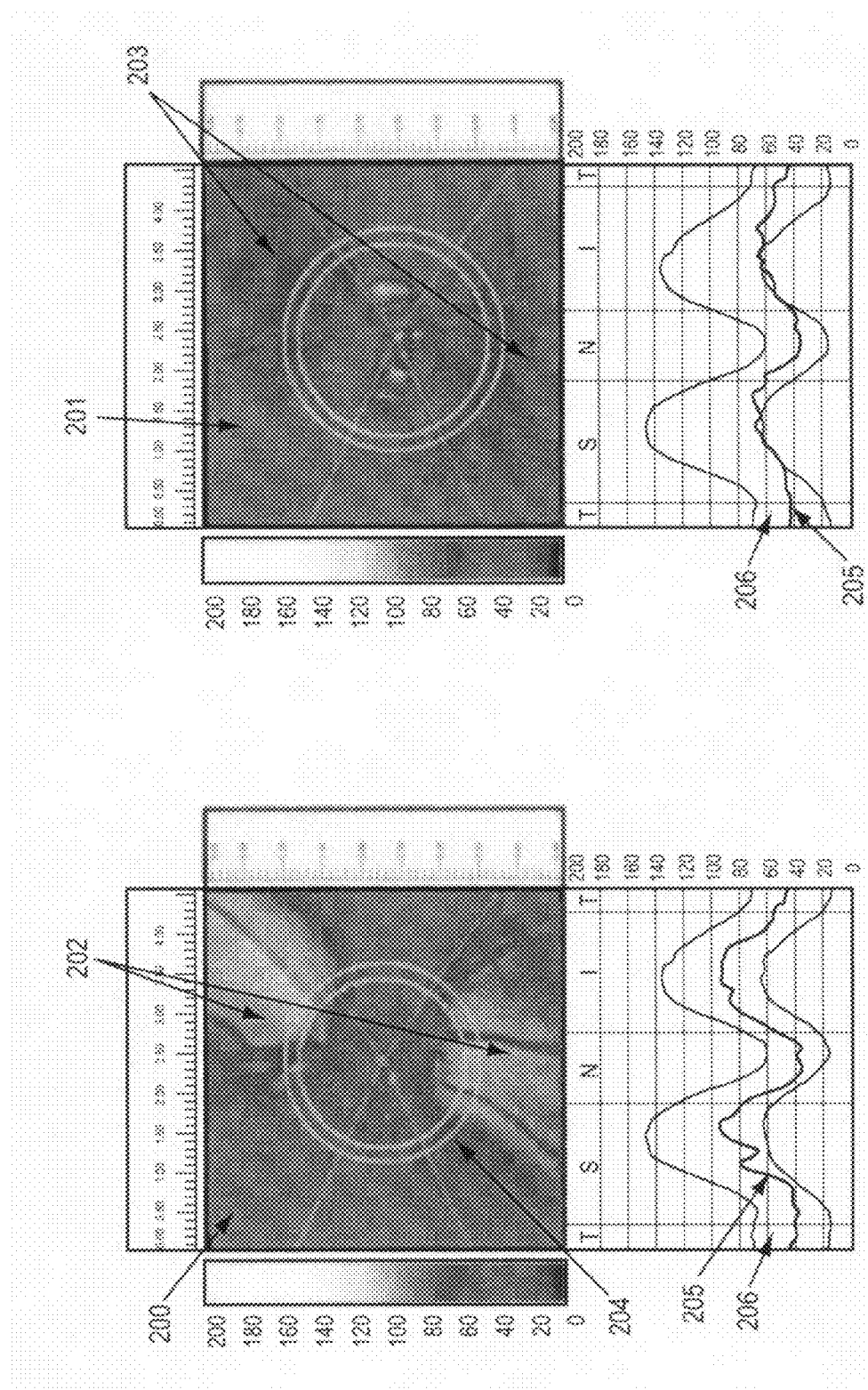
FIGS. 2A and 2B show RNFL thickness plots of early and late stage glaucoma, respectively, produced by the GDx technique.

FIGS. 2A and 2B show RNFL thickness maps 200 and 201 of the progression of an early stage glaucoma patient derived from a Polarimetry device GDx made by Laser Diagnosis Technologies, San Diego, Calif. (now been acquired by Carl Zeiss Meditec, Dublin, Calif.). The GDx technique measures the amount of polarization rotation in the light beam as the beam is scanned across the nerve head. The RNFL tissue is birefringent and therefore the amount of polarization rotation is a measure of the RNFL thickness.

RNFL thickness map 200 shown in FIG. 2A shows early stage glaucoma while RNFL thickness map 201 shown in FIG. 2B shows glaucoma at a later stage. The birefrigent characteristic of the RNFL caused the polarization of the incident beam to change its direction of polarization dependent on the thickness of RNFL through which it passes. By measuring the rotation angle of the polarization of the reflected beam, the relative RNFL thickness can be calculated. The superior and inferior RNFL bundle 202 of the early stage glaucoma patient's RNFL 200 is still very visible. But at late stage, the superior and inferior RNFL bundle 203 has become very thin in the RNFL map 201. Below image 200 and image 201, a variation of the RNFL thickness 205 is plotted along the perimeter of a conventionally chosen 3.45 mm diameter circle 204 centered on the nerve cup. A region of normal RNFL thickness 206 is shown in order to estimate the statistical risk based on the patient's measured RNFL thickness. However, the stereometric parametric values, e.g. disk and cup shapes, are not obtainable from this image method. Therefore, the usual diagnostic parameters obtained by determining the disk and cup shapes are unobtainable.

Figure 3:
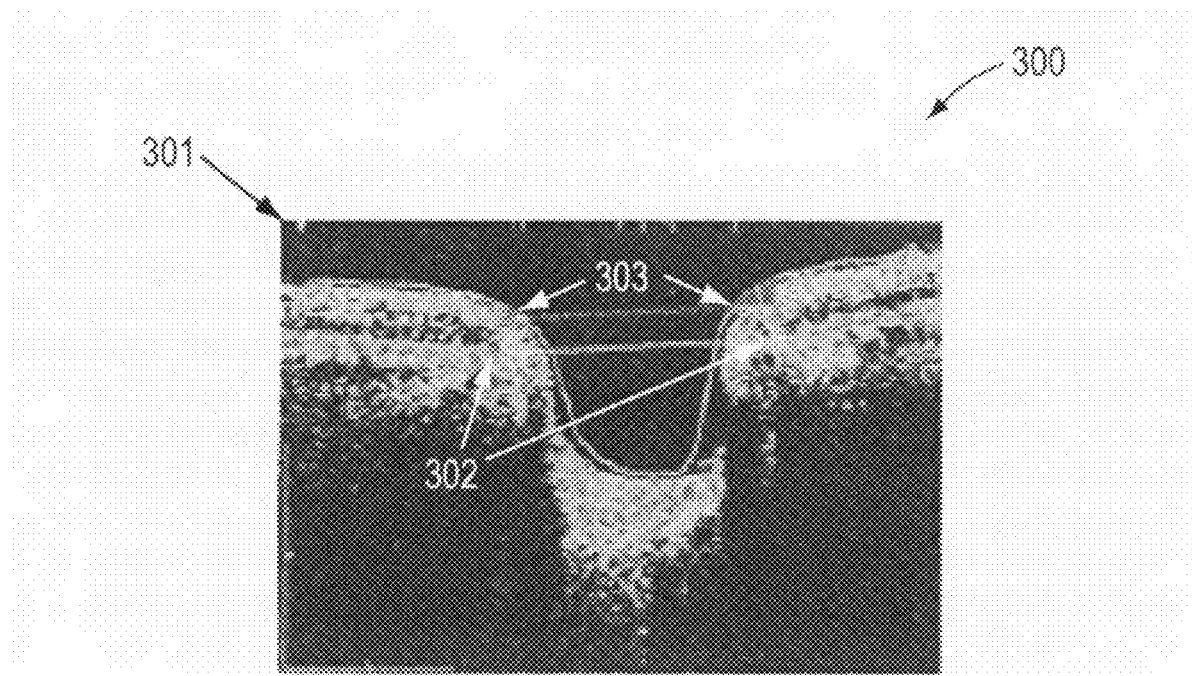
FIG. 3 shows an image of the nerve head taken by an OCT technique.
Figure 3:
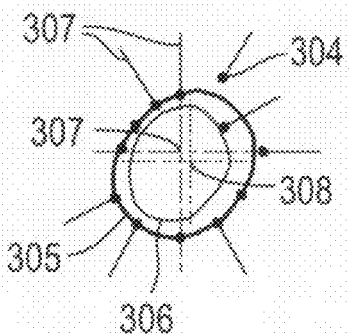

FIG. 3 shows a graphic display 300 of a nerve head morphology analysis obtained by using a Stratus™ OCT made by Carl Zeiss Meditec, Dublin, Calif. The Stratus™ OCT takes six cross-section OCT scans 307 across the nerve head. An image of one scan, scan 301, is shown in display 300. Both sides of disk margin 302 are identified. Disk margin 302 (also known as the edge of the retinal pigment epitheal (RPE)), as shown in scan 301, is identified by a change in density indicating the edge of the disk. Also visible in cross section 301 is the nerve fiber entering the cup. The cup margin 303 is conventionally defined by intersecting a reference line that is 150 μm above and parallel to the line connecting the sides of disk margin 302 with the nerve head inner most boundary, as illustrated in scan 301.

The disk contour 305 is then obtained by connecting the twelve disk margin points from each of the six cross-sectional scans 307. Similarly, the cup contour 306 is obtained by connecting the twelve cup margin points from each of the six cross-sectional scans 307.

In the current example, one of the disk margin points, point 304, is obviously not connected to the disk contour. This is typically caused by a blood vessel shadowing effect, which will be further discussed below. Another disadvantage to this technique is that due to the low number of landmarks, the scans are very difficult to be aligned to disk center 308. This can be demonstrated in image 300 because disk center 308 is not coincident with the center of scans 307.

As is demonstrated from the analysis of data obtained from each of these techniques, none of them provide a complete, reliable, or accurate analysis of the nerve head. Each of them fail to reliably determine one or more parameters.

Figure 11:
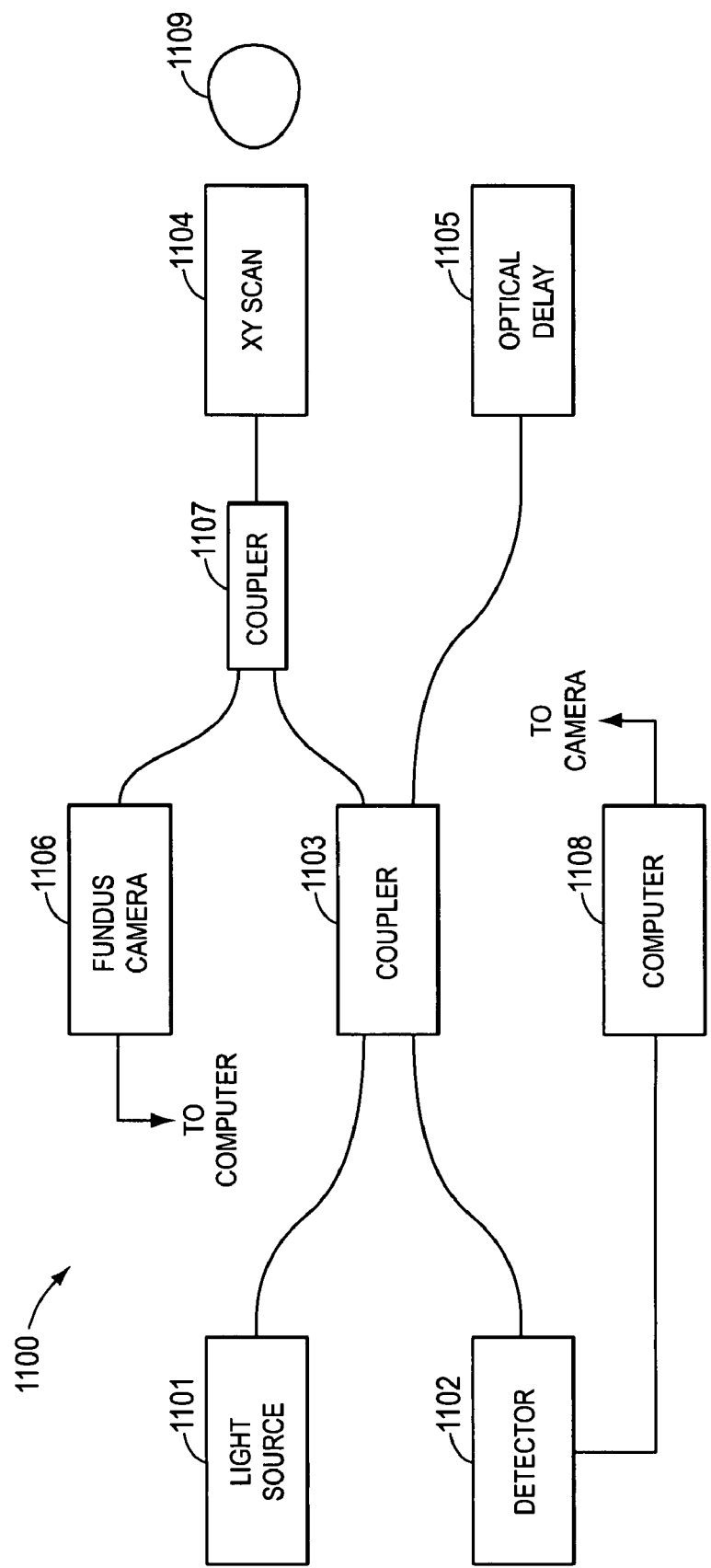
FIG. 11 illustrates an embodiment of an OCT imager that can be utilized to perform an eye examination according to some embodiments of the present invention.

Methods of retinal scanning according to some embodiments of the present invention can determine the parameters that characterize the nerve head while overcoming issues of eye movement and blood vessel placement. FIG. 11 illustrates an example of an OCT imager 1100 that can be utilized in eye examinations according to some embodiments of the present invention. OCT imager 1100 includes light source 1101 supplying light to coupler 1003, which directs the light through the sampling arm to XY scan 1104 and through the reference arm to optical delay 1105. XY scan 1104 scans the light across eye 1109 and collects the reflected light from eye 1109. Light reflected from eye 1109 is captured in XY scan 1104 and combined with light reflected from optical delay 1105 in coupler 1103 to generate an interference signal. The interference signal is coupled into detector 1102. OCT imager 1100 can be a time domain OCT imager, in which case depth (or A-scans) are obtained by scanning optical delay 1105, or a Fourier domain imager, in which case detector 1102 is a spectrometer that captures the interference signal as a function of wavelength. In either case, the OCT A-scans are captured by computer 1108. Collections of A-scans taken along an XY pattern are utilized to generate OCT images. An example of an OCT imager is described in U.S. Pat. No. 7,480,058, filed concurrently with the present application, which is herein incorporated by reference in its entirety.

In addition to the OCT imager 1100, an apparatus for eye examinations according to the present invention includes a camera 1106, which can be a fundus camera. Light from camera 1106 is coupled into the sample arm of OCT imager 1100 by a coupler 1107. Coupler 1107 prevents light from camera 1106 from entering coupler 1103 while directing reflected light from eye 1109 that originates from camera 1106 back into camera 1106. Computer 1108 receives and analyzes both the images from camera 1106 and the images from OCT imager 1100. Utilizing the combination of images, accurate and complete OCT images of the nerve head can be obtained.

Figure 4:
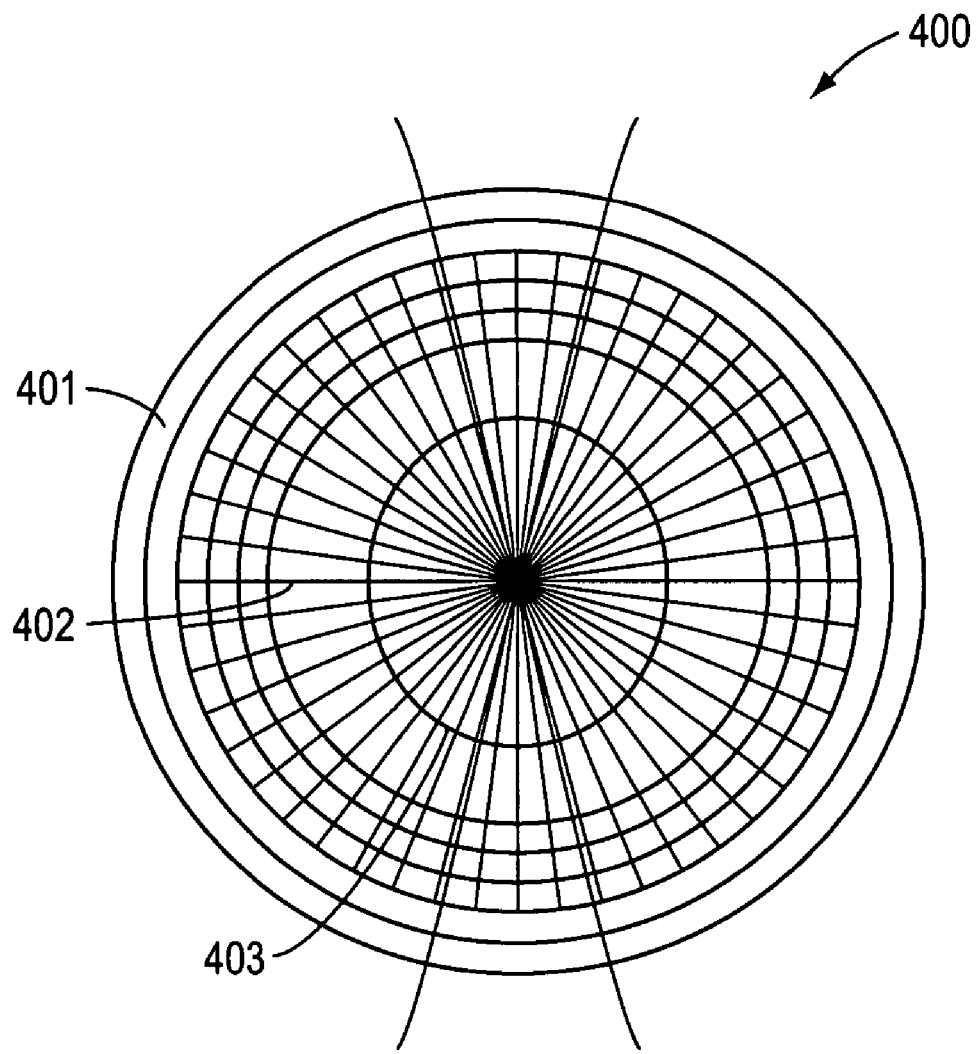
FIG. 4 shows a scan image pattern utilized in embodiments of the current invention for mapping the thickness of retinal nerve fiber layer around the disk and nerve head morphology.

FIG. 4 shows an OCT scan pattern 400 that can be utilized in embodiments of the present invention for better imaging the nerve head morphology and the retina nerve fiber layer (RNFL). Scan pattern 400 includes multiple concentric circular scans 401 and multiple radial line scans 402 centered at the center of concentric circular scans 401. Concentric circular scans 401 cover most, if not all, human eye nerve head (disk) size ranges The RNFL thickness just outside of disk margin 403, at the conventional 3.45 mm radius, has the most desired clinical information regarding a glaucoma patient's progressive loss of RNFL thickness.

Due to a patient's eye movement, however, it is very difficult to align scan 400 on the center of the patient's disk. However, scan pattern 400 need not be precisely positioned to the patient's disk. Scan pattern 400 is arranged such that the length of radial lines 402 overlap with the area covered by at least one of circular scans 401. As soon as scan pattern 400 is large enough to cover the region of interest, the acquired image then can be processed, as will be further discussed below, to determine the location of the center of the disk with the multiple radial line scans and select the data from the multiple circular scans to determine the RNFL thickness at the appropriate distance from and centered to the disk.

Figure 5:
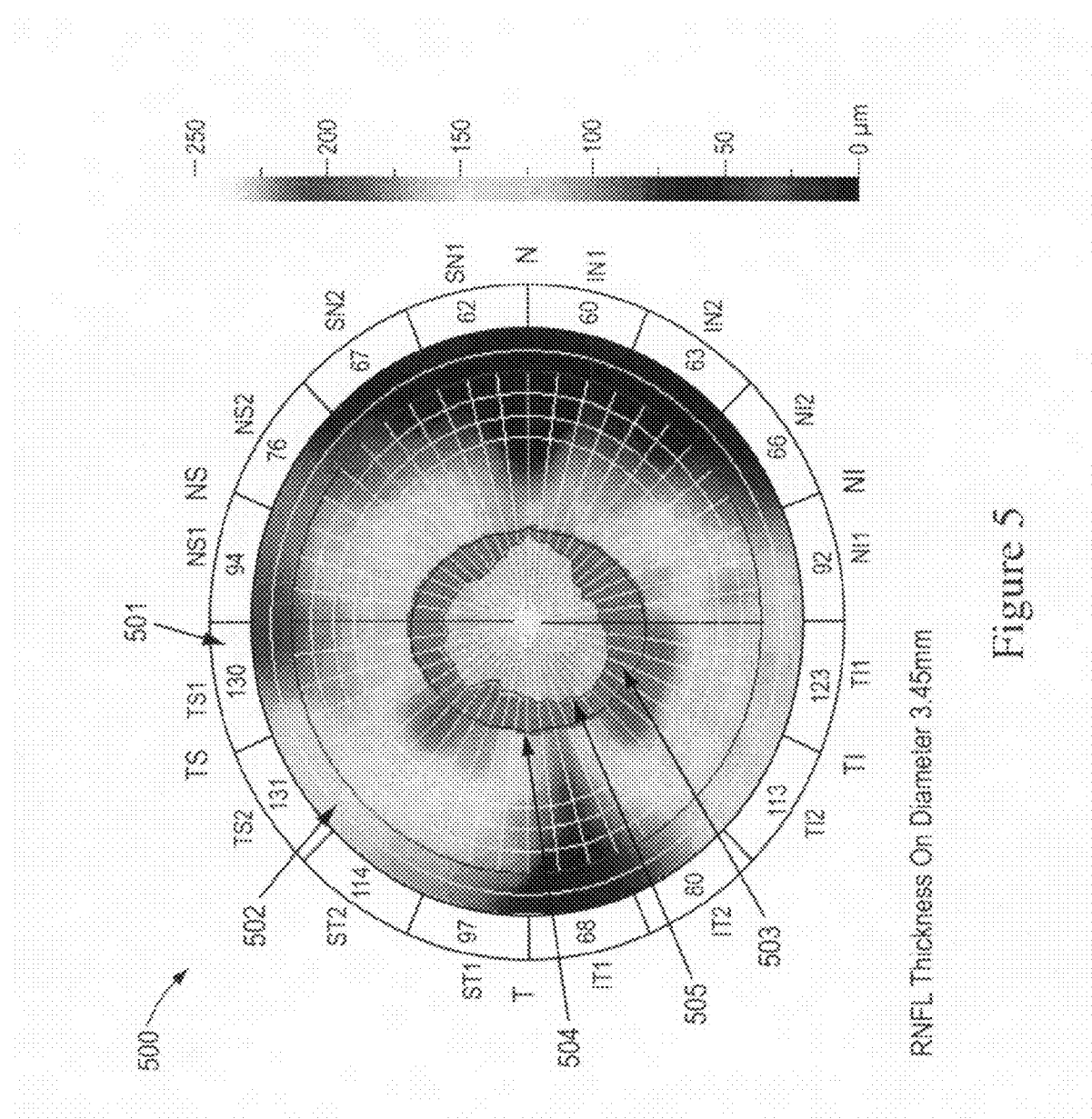
FIG. 5 shows an example graphic produced with an embodiment of the current invention to display the nerve head morphology related to a glaucoma diagnosis.

FIG. 5 shows an OCT image 500 taken with scan 400 of FIG. 4 according to some embodiments of the present invention. An average segment RNFL thickness in a circle with a diameter just outside of the disk margin, for example the conventional 3.45 mm, is shown in each segment 501 around the RNFL map 502. Rim area 503 is surrounded by disk margin contour 504 and cup boundary 505. In this single graphic plot, all critical clinic information about the nerve fiber in the disk region is simultaneously displayed for easy clinic diagnosis.

Previously, at least two independent systems are required to perform the Nerve fiber map and disk/cup contour separately to acquire the information shown in FIG. 5. For example, an Stratus™ OCT system (produced by Carl Zeiss Meditec, Dublin, Calif.) and a GDx system (produced by Laser Diagnosis Technology, San Diego, Calif.) or a HRT system (produced by Heidelberg Enginnering, Germany) and a GDX system.

However, due to absorption of the incident beam by blood vessels. The OCT signal will be very weak behind a blood vessel. Thus it causes a shadowing on the choroid tissue. Since the tip of choroid layer, which is also referred to as the retinal pigment epitheal (RPE) tip, is used to outline the disk margin, the disk shape based on an OCT image such as that shown in FIG. 5 is not reliable. Light absorption by blood vessels (also referred to as the blood vessel shadowing effect) is demonstrated in FIG. 6.

Figure 6:
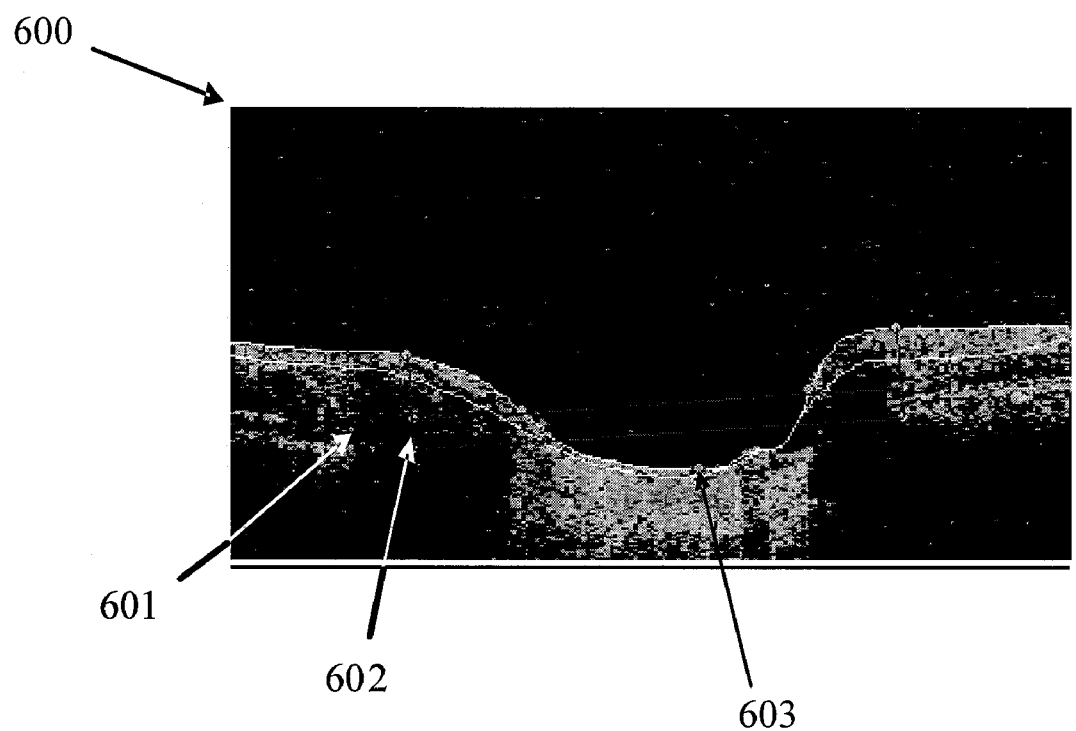
FIG. 6 shows an example of image distortion in an OCT scan caused by light absorption of the blood vessel tissue surrounding the nerve fiber disk.

FIG. 6 shows a cross-sectional OCT scan 600 across a nerve head. The disk margin 602 is shadowed by a blood vessel located directly above it, which is invisible in the OCT image itself. From OCT scan 600 alone, the boundary of choroid 601 may be mistakenly identified as the disk margin. If this erroneous point is utilized to determine the disk contour, the disk contour will be distorted.

Figure 7:
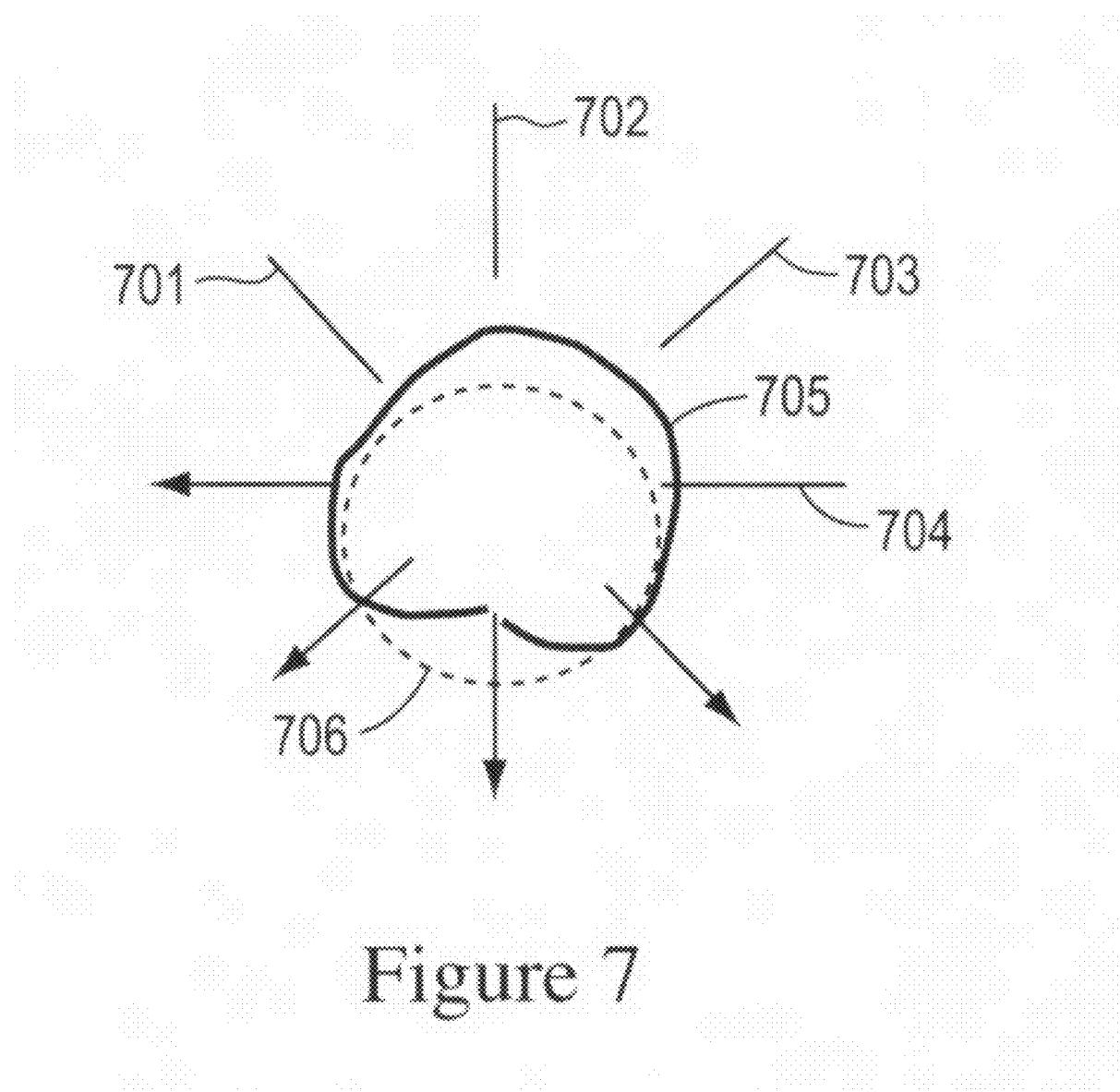
FIG. 7 shows an example of disk margin distortion caused by eye motion during the acquisition of the image.

Eye motion is another factor that cause mis-presentation of the disk morphology. The effects of eye motion are illustrated in FIG. 7. As illustrated in FIG. 7, a disk contour 706 is constructed from the disk margins derived from at least four radial OCT line scans, identified as scans 701, 702, 703, and 704 in FIG. 7. Due to the motion of the eye, scans 702 and 703 are shifted and their use results in a distorted disk contour 705.

Figure 10:
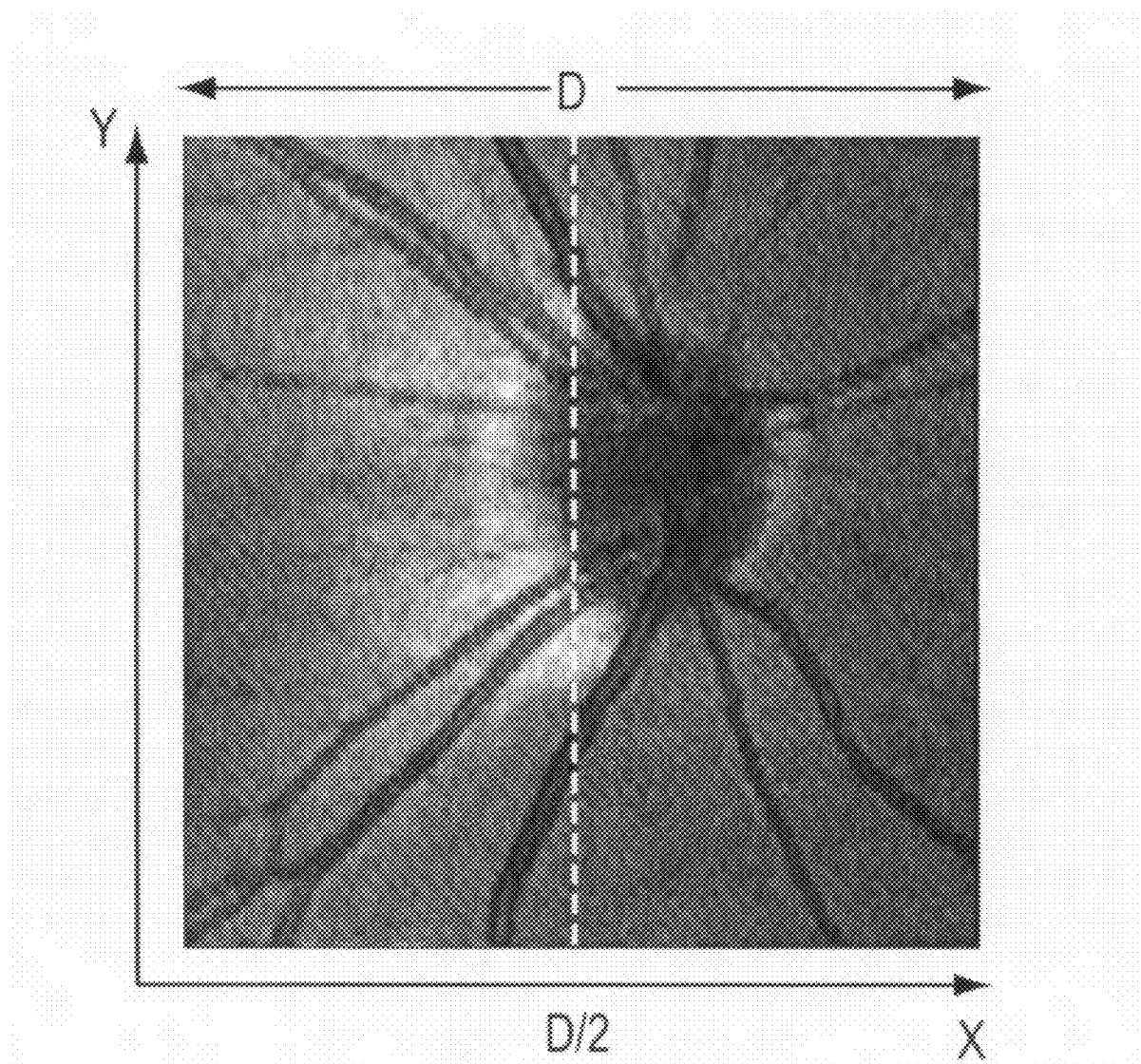
FIG. 10 illustrates a brightness compensation routine that can be utilized in some embodiments of the present invention.

To overcome these problems, an eye exam according to the present invention, as is illustrated in the imager shown in FIG. 10, uses a stream of video disk images, recorded during the acquisition period of the series of OCT scans, to realign the scan pattern of the disk morphology. Such a re-aligned scan image is shown in FIG. 5. A near infrared wavelength illumination is used to illuminate the retina during the OCT scan. The light reflected from the disk is very bright and the blood vessels are relatively invisible in these wavelength range. Therefore, the disk contour is well defined in the video image and show no obscuration of the blood vessels. The disk shape from the video image is then used to correct the tip of the choroid tissue (the RPE tip) by blood vessel shadowing. The retinal motion, detected from the stream of the video images, can be used to register the OCT images while scanning a pattern such as pattern 400 relative to each other in order to build an accurate composite OCT image.

Figure 8:
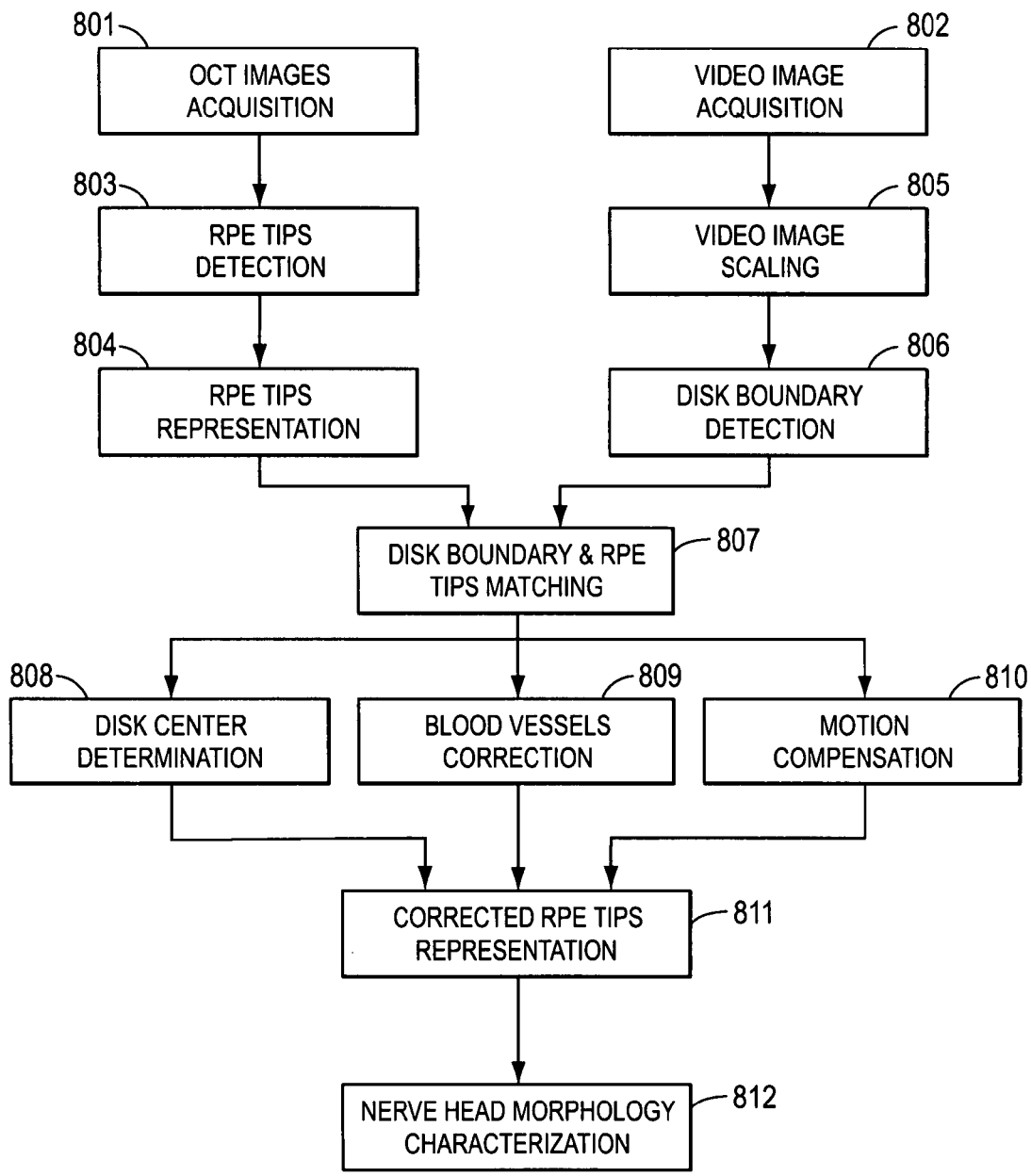
FIG. 8 shows a block diagram illustrating the steps of the automatic image processing method according to embodiments of the present invention.

FIG. 8 shows a block diagram illustrating the steps of the image processing method according to some embodiments of the present invention. The embodiment of image processing method according to the present invention includes the following steps: (1) OCT images acquisition step 801; (2) video image acquisition step 802; (3) retinal pigment epitheal (RPE) tips detection step 803; (4) RPE tips representation step 804; (5) video image scaling step 805; (6) disk boundary detection step 806; (7) disk boundary and RPE tips matching step 807; (8) disk center determination step 808; (9) blood vessels correction step 809; (10) motion compensation step 810; (11) corrected RPE tips representation step 811; and (12) nerve head morphology characterization step 812.

The first step in the image processing method of the present invention is the acquisition of OCT images in OCT images acquisition step 801. In some embodiments, the OCT images are acquired utilizing scan pattern 400 as shown in FIG. 4, although other scan patterns that are similarly rich in data can be utilized. The multiple radial line-scanned images are used to detect the locations of RPE tips, and subsequently to characterize the nerve head morphology. The multiple concentric circular-scanned images are used to detect the RNFL thickness outside the disk margin after disk boundary positions and their center being determined. Simultaneously with the acquisition of the OCT images, images are obtained with a video camera (such as camera 1006 in FIG. 10) in step 802. The video images, which may be fundus video images, will be used to guide the detection of RPE tips in OCT images.

Step 803 is the detection of RPE tips in the OCT images acquired in step 801. Based on edge detection of intensity changes along the vertical direction of the OCT images, RPE top edges are first extracted and then smoothed to form two RPE top curves, separated by the disk valley, shown as 603 in FIG. 6, for each OCT image. The starting points of the two RPE top curves are located at the first line and the last line of the OCT images, respectively. The ending points of the two RPE top curves are detected as the RPE tips. The RPE tips thus detected are not accurate in general because of blood vessel distortion and/or eye motion.

Each OCT image is acquired in a x-θ plane and therefore the RPE tips are detected and represented in the same x-θ plane. To best match with the disk contour in the video image subsequently, the RPE tips are transformed into an x-y plane representation in step 804 to arrive at a representation similar to that shown in FIG. 3. The number of contour points utilized in the x-y representation is double the number of radial line-scanned images acquired in step 801.

In step 805 the video images acquired in step 802 are scaled such that their x-y pixel resolution are identical to those of the x-y RPE tip representation of step 804. Step 805 matches the pixel resolutions of the OCT images and video images, which in general are different.

In step 806, disk boundary detection from the video image is performed. An adaptive threshold algorithm can be used to segment the disk area from its background and to extract the boundary curve.

In step 807, the RPE tips determined in step 804 are matched with the disk boundary curve determined in step 806. In other words, each lateral OCT scan resulting in identification of RPE tips in step 804 is paired with points on the disk boundary curve determined in step 806.

The disk center can be computed by the center of gravity, or the geometric center, of the disk boundary curve. However, the aiming center, where scan pattern 400 is centered, may not be coincided with the disk center. Assuming an aiming center position $(x_a, y_a)$ at the video image and a given scanning angle θ, two distance measures from the corresponding boundary points to the aiming center can be determined. These measures would be matched well with the distance measures computed through OCT images, if there were no blood vessel distortion and/or eye motion. The blood vessel distortion causes the distance measure to become larger since the RPE tips would be incorrectly detected at farther positions from the image center, as illustrated in FIG. 6. Nevertheless, the distortion is expected to be local in the sense that the distance enlargement may occur for only one RPE tip instead of both RPE tips in an OCT image. Besides, the distance enlargement is not smooth in general across consecutive images. In contrast, the incorrectly detected positions of RPE tips caused by eye motion would behave much differently. First, the distortion is expected to be global in the sense that the distance modification will always occur for both RPE tips in an OCT image. Because eye motion will cause both RPE tips to move in the same direction, meaning that if one RPE has distance enlargement, then the other should have distance shrinkage, as one is moving apart from the image center, and the other is moving closer to the image center. Secondly, the distance enlargement and shrinkage is smooth across consecutive images. A preferred matching scheme based on these observations is used to compute the positional offsets of RPE tips caused by blood vessel distortion and/or eye motion.

The disk center is determined by the geometric center of the disk boundary curve in the video image in step 808, usually after the corrective steps 809 and 810 have been performed. The determination of disk center is important in displaying preferred clinic information, as previously described with respect to FIG. 5. The local RPE tips positional offsets caused by blood vessel distortion were determined in the aforementioned matching process, and RPE tips can be re-positioned to correct the local offsets at step 809. The global RPE tips positional offsets caused by eye motion were also determined by the aforementioned matching process, and RPE tips can be re-positioned to compensate the global offsets in step 810. These steps effectively resolve three fundamental issues whose solution was previously absent in nerve head imaging systems: Namely, the incapability to accommodate disk center determination, blood vessel distortion, and eye motion simultaneously.

In step 811, the corrected RPE tips in the x-y plane according to the positional offsets previously computed is determined. Based on the correct positions of RPE tips, the nerve head map and its morphological characterization, as previously described with respect to FIGS. 4 and 5, can be more accurately performed in step 812.

Although many of the steps shown in FIG. 8 are performed automatically by a computer, some of the steps may be performed or assisted by an operator. For example, step 806 of disk boundary detection may use operator input. Additionally, RPE Tip detection may utilize operator input. In some embodiments, all of the steps are performed by a computer.

The embodiment shown in FIG. 8 illustrates utilizing video images in order to correct the RPE tips determined from the individual OCT images obtained in step 801. However, other images can also be utilized in embodiments of the present invention. For example, a separate OCT image can be taken with a very dense scan pattern, for example a raster scan pattern, prior to acquisition of OCT images in step 801 with the scan pattern of FIG. 4. The dense OCT image can be utilized to create a template OCT image, in which the disk contours are identified. This template OCT image can replace the video images taken in step 802 and the RPE tips are matched to the boundary identified in the template OCT image in step 807. One advantage to this technique is that the template OCT image can be re-used on subsequent visits by that patient.

Figure 9:
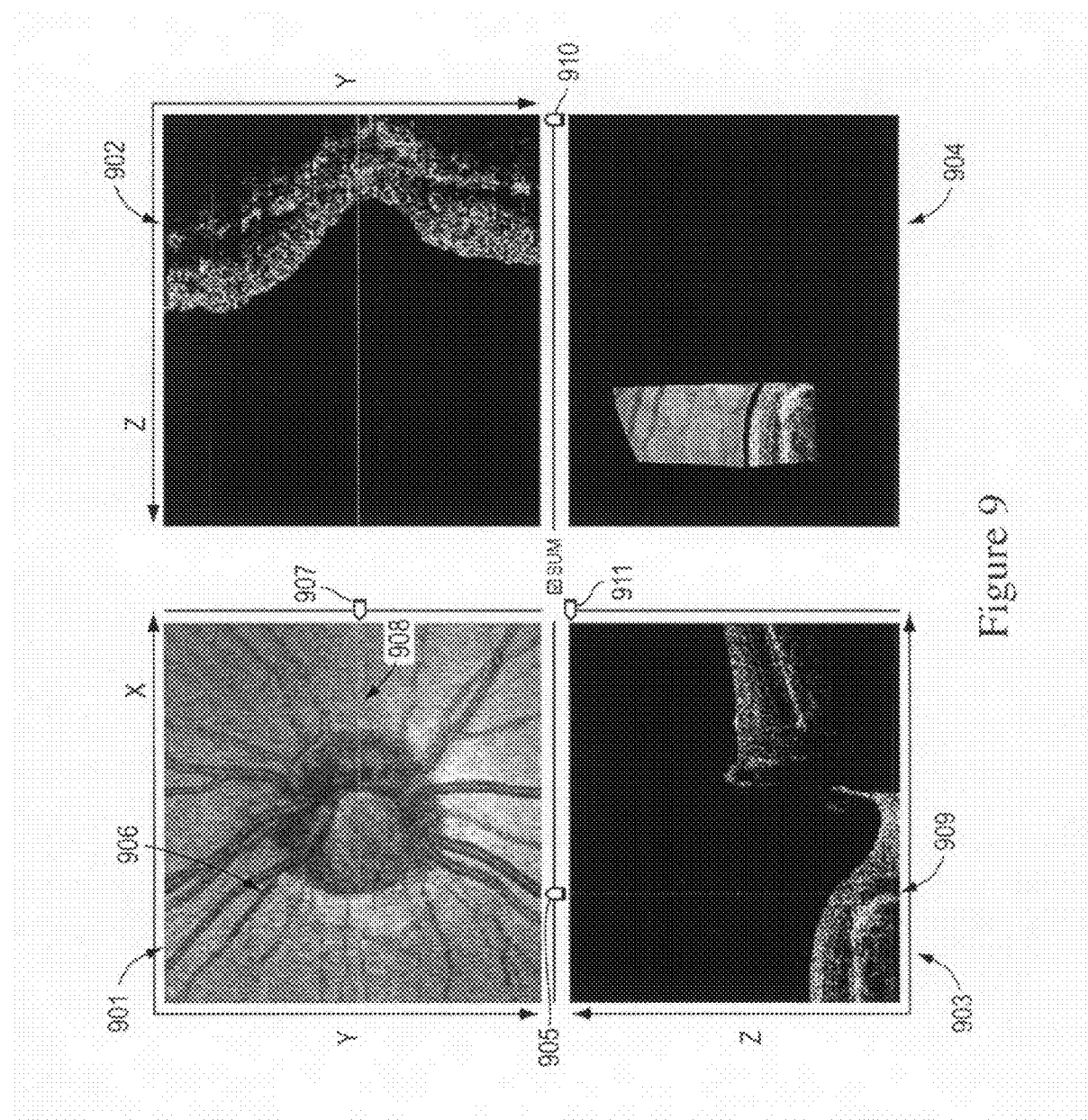
FIG. 9 shows a scan pattern and graphic display according to embodiments of the current invention for mapping the nerve head boundary.

FIG. 9 shows a template OCT scan where the nerve head boundary has been determined. In the image shown in FIG. 9, a raster line scan pattern is used to generate a three dimensional data set of the nerve head region. For example, a 4 mm by 4 mm area can be scanned with 100 frames of OCT images and each OCT cross sectional image can be composed with 512 axial scans. The number of frames scanned in the Y direction can be increased to enhance the image resolution with the trade-off of longer scan time and more eye motion artifact.

The OCT scan data is then recomposed in a three dimensional manner $(x_i, y_i, z_i)$ An enfaced image of the nerve head 901, as shown in FIG. 9, is the sum of signals in the Z-direction for each pixel in $(x_i, y_i)$, or $$Z_{sum} = \Sigma z_i (i=k,j),$$

where k and j can be adjusted to achieve enface image to reveal the nerve head boundary. The adjustment can be done by an operator with manually adjustable slides 910 and 911, or the adjustment can be determined with algorithm that the best contrast is achieved on the boundary.

To enhance the nerve head boundary contrast, the anterior surface of the retinal can be segmented out with image processing algorithms by various methods. One method according to some embodiments of the present invention is to examine enface image in the plane that is parallel to RPE layers. The sum of signal from layer k to layer j can be adjusted so that the nerve head boundary contour found in the enfaced image has a close correlation with the RPE tips found in the cross sectional image in the X-Z plane.

Because the nerve head is normally tilted to the temporal direction. The OCT signal strength is normally weak in the nasal side of the retina. To enhance the enface image contrast and uniformity, it is advantageous to level out the imbalance image brightness first before finding the nerve head boundary. Various methods are known for balancing the brightness. One such method that can be utilized in embodiments of the present invention, which is illustrated in FIG. 10, is as follows: Compute F1 and F2 for the x direction from $$F1 = \text{average of } f(x,y) \text{ for } x < 2/D$$

$$F2 = \text{average of } f(x,y) \text{ for } x > 2/D$$

where f is the brightness as a function of x and y and D is the extent of the display. The difference in brightness can then be calculated as $$\Delta f = F1 - F2.$$

A correction factor can then be determined as $$K = \Delta f / (D/2).$$

The signal strength of the entire OCT image in the X-Y plane in the x direction can then be computed as $$f'(x, y) = f(x, y) - xK.$$

The nerve head boundary can be either segmented out by the above algorithm automatically, or be drawn by operator with the assistance view 903. The nerve head boundary is shown as RPE tips in the cross sectional view in 903. The tips in some scan will be shadowed by the retinal blood vessel above it. The black region in enface image 901 clearly indicates where the RPE tips are located. An operator can view each cross sectional image by sliding the lines 906 and 908 with slider 905 and 907.

After confirming the boundary locations for each cross sectional image, the two RPE tip locations will be recorded and displayed in enface image 901. The operator can then repeat this process for each cross sectional image until enough data points are acquired to completely identify the nerve head boundary on enface image 901. Because there are enough cross sectional images, the operator can skip the ones where it is unclear where the RPE tips are located and still be able to find the RPE tips in the neighboring regions. The nerve head boundary can then be determined with sufficient accuracy. The operator can also perform the same process with cross sectional images in Y-Z plane 902. The 3D image 904 is the corresponding image of cross sectional image in 901, 902, and 903.

The nerve head boundary normally does not change for glaucoma patients, so the boundary contours can be saved as a baseline. This method is similar to that utilizing video baselines, described in FIG. 8, however it is drawn from OCT images alone with operator input.

For the next patient visit, an enface image with baseline contour can be used as the reference to find out the nerve head boundary on the new scans. The retinal blood vessel has very high contrast in the enface image and it normally does not change location in glaucoma patients. A cross correlation algorithm can be used to register the new scan with the baseline enface image. After the enface image is aligned with the baseline enface image, and the nerve head boundary baseline can be overlaid to the enface image from the new scans and the nerve head boundary in the new enface image can be drawn by the algorithm. From these baseline boundary contours, algorithms can be utilized to find RPE tips within a limited range close to the predetermined pixel in X-Y plane and process already described in part of FIG. 8.

The nerve head boundary baseline determined in FIG. 9 can be utilized to replace the video images taken in step 802 and processed in steps 805 and 806. Although RPE tips from OCT images taken in step 801 of FIG. 8 can not be corrected for eye motion utilizing this method, correction for blood vessels and disk center determination can be accomplished. Because of the speed in acquisition of OCT images with scan pattern 400 of FIG. 4, eye motion may, in some cases, be neglected during the examination.

Although an embodiment of an imaging method according to the present invention has been described above, it will be understood that the invention is not limited to the embodiments disclosed, but is capable of numerous rearrangements and modifications of parts and elements without departing from the spirit of the invention. The embodiments described above are exemplary only and are not meant to be limiting in any way. One skilled in the art may recognize numerous modifications that can be made in the systems described. These modifications are meant to be within the scope of this disclosure. As such, the invention is limited only by the following claims.

What is claimed is:

1. A method of eye examination, comprising:
    acquiring OCT images corresponding to a scan pattern, wherein the scan pattern substantially covers a nerve head region;
    the scan pattern includes a plurality of concentric circles and a plurality of radial lines intersecting at the center of the concentric circles and intersecting at least one of the concentric circles;
    determining optical disk boundary points from the OCT images;
    matching the optical disk boundary points with the optical disk boundary determined from one or more separate template images;
    correcting the optical disk boundary points; and
    determining at least one nerve head morphology characterization.

2. The method of claim 1, wherein correcting the optical disk boundary points includes performing a blood vessel correction.

3. The method of claim 1, wherein correcting the optical disk boundary points includes determining an optical disk center.

4. The method of claim 3, wherein determining at least one nerve head morphology characterization includes determining retinal nerve fiber layer thickness in a circle centered on the optical disk center.

5. The method of claim 1, wherein the one or more template images are video images taken simultaneously with the OCT images.

6. The method of claim 5, wherein correcting the optical disk boundary points includes correcting for eye movement.

7. The method of claim 1, wherein the one or more template images is a template OCT image taken with a raster scan pattern.

8. The method of claim 7, wherein a nerve head boundary is determined in the template OCT image.

9. The method of claim 1, wherein the scan pattern spans an area large enough to encompass the nerve head region.

10. The method of claim 1, wherein a retinal nerve fiber layer thickness is calculated at a particular diameter circle centered on the nerve head.

11. The method of claim 5, wherein the video images are acquired with near IR light.

12. The method of claim 5, further including determining an optical disk boundary in each of the video images.

13. The method of claim 12, wherein determining the optical disk boundary is performed automatically.

14. The method of claim 12, wherein determining at least one of the optical disk boundaries is performed by an operator.

15. The method of claim 8, wherein the nerve head boundary is determined by
    forming an enface image from the template OCT image;
    determining the boundary contour from the enface image.

16. The method of claim 1, wherein one or more of the separate template images used corresponds to a 3D data set collected using a dense OCT raster scan comprising the optical nerve head region.

17. The method of claim 16, wherein forming an enface image further comprises:
    adding data from a plurality of layers at different depths in the three-dimensional OCT scan; and
    adjusting the different layers used to form the enface image to find a close correlation between the nerve head boundary contour and the retinal pigment epithelial RPE tips found in the cross sectional images obtained from the OCT scans.

18. The method of claim 15, wherein determining the boundary from the enface image further comprises:
    saving the boundary contours as a baseline; and
    using a cross correlation algorithm to register a new OCT scan with the enface image having a baseline boundary contour.

* * * * *